(12) United States Patent
Björling et al.

(10) Patent No.: US 7,778,697 B2
(45) Date of Patent: Aug. 17, 2010

(54) DETECTION OF ISCHEMIA

(75) Inventors: Anders Björling, Järfälla (SE); Kjell Norén, Solna (SE)

(73) Assignee: St. Jude Medical AB, Jarfalla (SE)

(*) Notice: Subject to any disclaimer, the term of this patent is extended or adjusted under 35 U.S.C. 154(b) by 768 days.

(21) Appl. No.: 11/667,505

(22) PCT Filed: Oct. 11, 2004

(86) PCT No.: PCT/SE2004/001444

§ 371 (c)(1), (2), (4) Date: May 10, 2007

(87) PCT Pub. No.: WO2006/041337

PCT Pub. Date: Apr. 20, 2006

(65) Prior Publication Data

US 2009/0143690 A1    Jun. 4, 2009

(51) Int. Cl.
A61B 5/02    (2006.01)

(52) U.S. Cl. ........................ 600/509; 600/508

(58) Field of Classification Search ............... 600/509, 600/508, 507
See application file for complete search history.

(56) References Cited

U.S. PATENT DOCUMENTS

| | | |
|---|---|---|
| 5,159,932 A | 11/1992 | Zanetti et al. |
| 5,891,045 A | 4/1999 | Albrecht et al. |
| 6,016,443 A | 1/2000 | Ekwall et al. |
| 6,233,486 B1 | 5/2001 | Ekwall et al. |
| 6,256,538 B1 | 7/2001 | Ekwall |
| 6,264,606 B1 | 7/2001 | Ekwall et al. |
| 6,768,919 B2 | 7/2004 | Starobin et al. |

FOREIGN PATENT DOCUMENTS

| | | |
|---|---|---|
| EP | 1 384 433 | 1/2004 |
| WO | WO 03/020367 | 3/2003 |

*Primary Examiner*—Carl H. Layno
*Assistant Examiner*—Jon-Eric C. Morales
(74) *Attorney, Agent, or Firm*—Schiff Hardin LLP

(57) ABSTRACT

In an ischemia detection method, and in an ischemia detector and a cardiac stimulator embodying an ischemia detector, a workload of a patient is measured, as is an ejection fraction (EF) associated with the heart of the patient is determined. A predetermined reference relation between EF and workload for the patient is stored, and an analysis unit detects a state of ischemia of the patient from deviation in the determined EF for various workloads from the stored reference relation.

25 Claims, 3 Drawing Sheets

DETECTION OF ISCHEMIA

BACKGROUND OF THE INVENTION

1. Field of the Invention

The present invention relates to an ischemia detector of the type having a workload sensor for sensing the workload of a patient. The invention also relates to a heart stimulator including such a detector and a method of detecting ischemia.

2. Description of the Prior Art

Cardiac ischemia is a condition related to lack of blood flow and oxygen to the heart muscle. Such a condition arises when a coronary artery is narrowed or occluded for a short time such that flow of oxygen-rich blood to the heart is reduced or prevented. If the ischemia is severe or lasts for too long time, it can cause a heart attack (myocardial infarction) and can result in heart tissue death.

A temporary blood shortage to the heart causes, in most cases, pain or angina pectoris, but in some cases the patient feels nothing. The latter case is called silent ischemia.

Angina usually occurs when the heart's need for blood exceeds the supply of blood. For example, running to catch a bus could trigger an attack of angina while walking might not. An angina might occur during exercise, strong emotions or extreme temperatures. Persons having a coronary artery spasm may have angina even when resting.

For persons suffering from an unstable angina, the chest pain is unexpected and usually occurs while the persons are resting. Inflammation, infection and secondary causes can also give rise to unstable angina. The cause of a form of unstable angina called variant or Printzmetal's angina is coronary artery spasm. Unstable angina is an acute coronary syndrome and should be treated as an emergency.

Persons having angina in addition may have also undiagnosed episodes of silent ischemia. Silent ischemia may also cause disturbances in the heart rhythm. Abnormal rhythms, like ventricular tachycardia or ventricular fibrillation, can interfere with the heart's pumping ability and cause fainting or even sudden cardiac death. A silent ischemia can lead to a heart attack without any prior warning. Detection of silent ischemia is consequently very important. Heart muscle disease (cardiomyopathy) caused by silent ischemia is among the more common causes of heart failure.

Silent ischemia is very common. The American Heart Association estimates, for instance, that 3 to 4 million Americans have episodes of silent ischemia. Especially persons who have had previous heart attacks and those who have diabetes are in the danger zone for developing silent ischemia.

Angina is a signal from the heart muscle of insufficient oxygen supply to the heart tissue due to diminished blood supply. A heart attack is the most extreme state of oxygen deprivation, in which whole regions of heart muscle cells begin to die because of lack of oxygen. The ejection fraction is often very low in the acute stage.

Even a heart attack may not be unbearably painful at first, permitting its victim to delay seeking treatment for as much as 4 to 6 hours after onset of the attack. By then the heart may have suffered irreversible injuries.

The longest running heart study, the Framingham Heart Study in United States, indicates that about one heart attack of four produces no symptoms, or at least no symptoms which the victim associates with a heart problem.

So-called silent heart attacks are only the most extreme case of the still more prevalent condition silent ischemia described above. The prevalence of silent heart attacks is high for elderly and diabetic patients.

U.S. Pat. No. 6,016,443 describes an ischemia detector including a detecting unit which identifies a state of ischemia as existing upon the occurrence of a predetermined relation between sensed repolarization and sensed workload of the patient.

U.S. Pat. No. 6,233,486 discloses an ischemia detector, wherein an ischemia is detected from an established relation between the systolic pressure of a subject and the subject's heart rate. It is mentioned that the described technique is useful for detecting also so-called silent ischemia.

In U.S. Pat. No. 6,256,538 an implantable heart stimulator with an ischemia detector is described, wherein the stimulation rate is reduced in response to the detection of ischemia. It is suggested to detect ischemia in one of the following ways, by analysis of recorded IEGMs or ECGs, by analysis of ST segments and T-waves, by analyzing measured AC impedance in a ventricle, by measuring sound absorption in heart tissue, by comparing measured differences between systolic and diastolic pressures from consecutive heartbeats, or by measuring cardiac output. The possibility to detect silent ischemia with these techniques is also mentioned.

U.S. Pat. No. 6,264,606 discloses an ischemia detector wherein an ischemia is identified upon the occurrence of a predetermined relation between sensed workload and sensed breathing activity, said predetermined relation meaning a sensed low workload and a simultaneously sensed high breathing activity.

SUMMARY OF THE INVENTION

An object of the present invention is to provide an improved technique for detecting ischemia.

The present invention is thus based on the fact that the ejection fraction, EF, of a patient drops suddenly when a certain patient dependent workload level is reached. A high cardiac rate then causes the diastolic phase to shorten, which decreases the flow of oxygen and energy to the myocardial cells as this flow is supplied during diastole. The lack of oxygen, energy etc. results in decreased cardiac performance—some cells fail to participate in the cardiac contraction—and EF decreases. The invention is based on the insight to track EF as a function of the workload of the patient and detect sudden drops of EF when increasing the workload level as compared to a stored predetermined reference relation between EF and workload. This reference relation which is patient specific has been determined previously, when the patient did not yet have signs of ischemia. The invention is also well suited for detecting silent ischemia which is an important advantage, since silent ischemia is extremely common as mentioned above.

A surrogate of EF can be obtained by different methodologies, and several different kinds of EF sensors can be used for sensing a parameter suitable for EF determination. Thus according to an advantageous embodiment of the detector according to the invention the EF sensor comprises a CMES sensor. A CMES-Sensor, Cardio Mechanical Sensor, is a piezoelectric sensor, the output signal of which contains both electric and pressure information. The pressure information thus received includes several components. In a certain frequency range the sensor is sensible to e.g. sound, i.e. it works as a microphone. The signal also contains the true pressure, pressure changes or the time derivative of the pressure. By suitable filtering of the sensor signal valve openings and closings can be detected, since a valve closing is associated with a significant pressure increase and sounds. An ordinary pressure sensor can be used as EF sensor or the EF sensor can comprise a photo-plethysmograph as well according to other advantageous embodiments of the detector according to the invention.

In other embodiments of the detector according to the invention the EF sensor is an impedance measuring unit that measures the impedance across the patient's heart. The impedance measuring unit preferably has leads intended for implantation into the patient's heart. Since blood and tissue have different conduction properties, the impedance measured across the heart will be different depending on the blood filling of the heart. The amplitude of an impedance signal measured in this way can consequently be used as an EF surrogate.

In other embodiments of the detector according to the invention the workload of the patient is measured by a sensor in the form of an accelerometer, or a minute ventilation (minute volume) determining unit, or a P-wave rate detector, or an arrangement that determines metabolic demand of the patient. Also combinations of measurements by these measuring devices can be used for determining the workload. To be able to determine the workload from the measured P-wave rate, a healthy SA (sinoatrial) node is required.

In another embodiment of the detector according to the invention a derivative former determines the derivative of EF with respect to workload, and a derivative comparator compares this derivative with a predetermined derivative reference value. This is an efficient way of finding sudden drops of EF.

In other embodiments of the detector according to the invention the EF determining unit determined onset of QRS and opening and closing of the aortic valve, and the EF determining unit preferably determines left ventricular ejection fraction LVEF from one of the following equations $$LVEF=0.84-0.64*PEP/LVET$$

$$LVEF=1.125-1.25*PEP/LVET$$

where PEP denotes the pre-ejection period from onset of QRS to opening of the aortic valve, and LVET the left ventricular ejection time from opening to closing of the aortic valve. Onset of QRS and opening and closing of the aortic valve can be determined with the above-mentioned CMES-sensor, other pressure sensors, or from the impedance signal.

In another embodiment of the detector according to the invention an alerting unit is provided for alerting a physician or clinic or the patient himself or herself in response to detection of an ischemia. For this purpose a telemetry arrangement is needed. For patients having silent ischemia, who consequently do not feel anything from his or her disease, it is of great value to be warned in this way.

The invention also relates to a heart stimulator embodying a detector according to the invention and stimulation controlling circuitry for controlling the delivery of stimulation pulses to a patient's heart in response to the detection of an ischemia. A patient experiencing ischemia needs to prolong the period of diastole to increase the flow of blood to the cardiac cells. Appropriate actions could therefore be to decrease the stimulation base rate, decrease the maximum tracking rate, making the rate responsiveness less aggressive, etc. The changes could, either be permanent or reset after a certain period of time. In an implantable cardioverter defibrillator parameters of ventricular tachycardia and ventricular fibrillation detection could also be changed to make it more sensitive, as ischemia sometimes precedes arrhythmic events.

DESCRIPTION OF THE PREFERRED EMBODIMENTS

Figure 1:
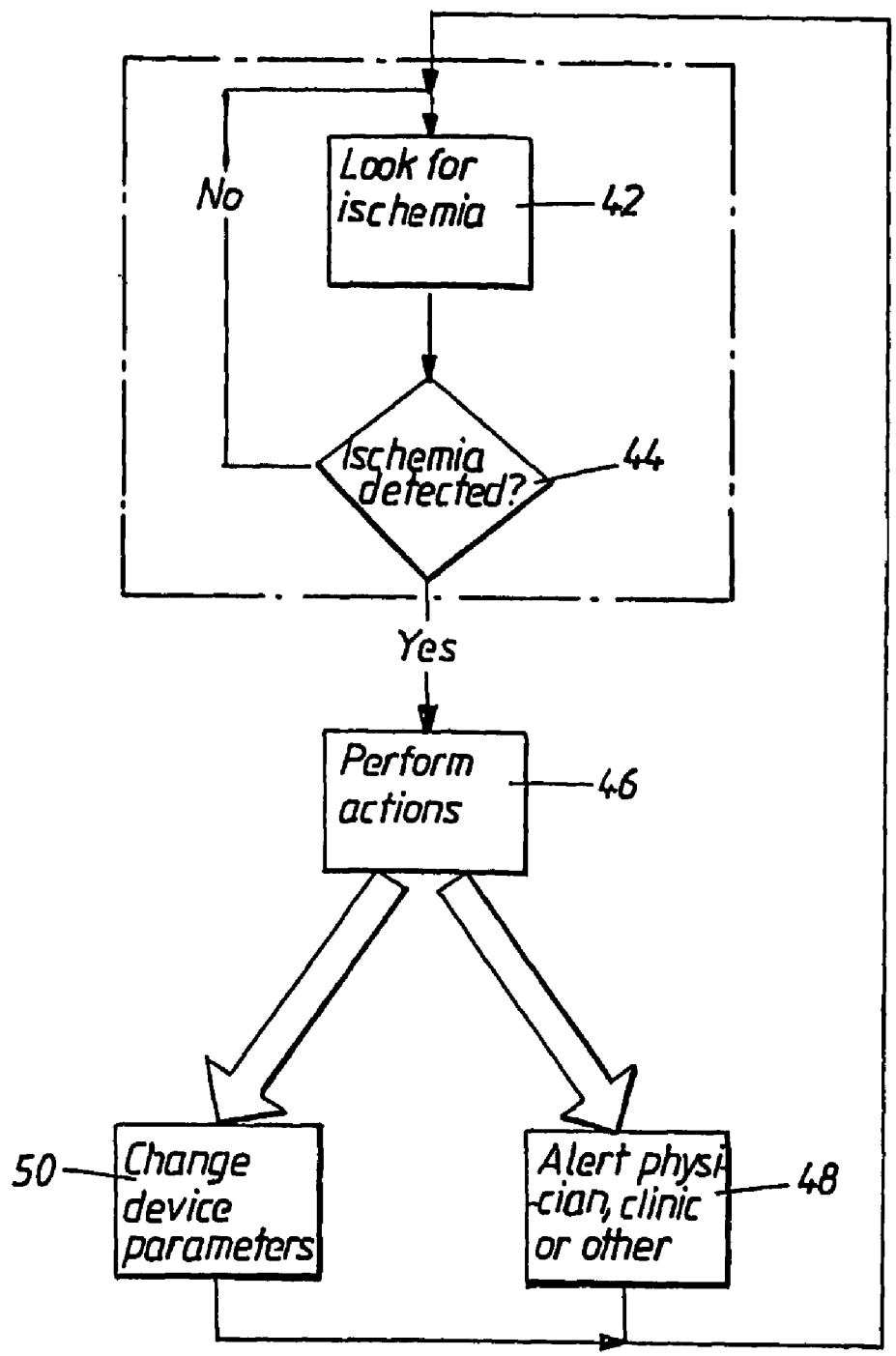
FIG. 1 is a flow chart of a basic procedure for detecting ischemia and performing actions upon detection of ischemia.

FIG. 1 is a flow chart of an overview of detecting ischema and performing actions upon detection. Thus an ischemia is looked for, at 42, If an ischemia is detected, at 44, suitable actions are performed, at 46. These actions can be alerting a physician, a clinic or simply storing the detected event in a database storing patient diagnostics, at 48. Suitable actions can also include alerting the patient him- or herself to come under medical treatment as soon as possible, and maybe also instruct the patient not to drive him- or herself to the emergency room. This is a very important feature for patients suffering from a silent ischemia, viz. patients who are not feeling anything of the detected ischemia.

Another example of suitable actions is to change parameters of a heart stimulator of the patient, at 50 in FIG. 1. A patient experiencing ischemia needs to prolong the period of diastole to increase the flow of blood to the cardiac cells. Appropriate actions could therefore be to decrease the stimulation base rate, decrease the maximum tracking rate, making the rate responsiveness less aggressive, etc. The changes could either be permanent or reset after a certain period of time. In an implantable cardioverter defibrillator parameters of ventricular tachycardia and ventricular fibrillation detection could also be changed to make it more sensitive, as ischemia sometimes precedes arrhythmic events. If such parameters are changed—permanently or temporarily—this must be recorded and communicated to the physician by means of the programmer at next follow-up.

According to the invention the detection of ischemia is based on the fact that EF of the patient drops suddenly when a certain workload level is exceeded by the patient. The high cardiac rate reached then causes the diastolic phase to shorten and this results in a decreased flow of oxygen and energy to the myocardial cells, as this flow is supplied during diastole. The lack of oxygen, energy, etc decreases the cardiac performance, i.e. some cells fail to participate in the cardiac contraction, and EF decreases.

Figure 2:
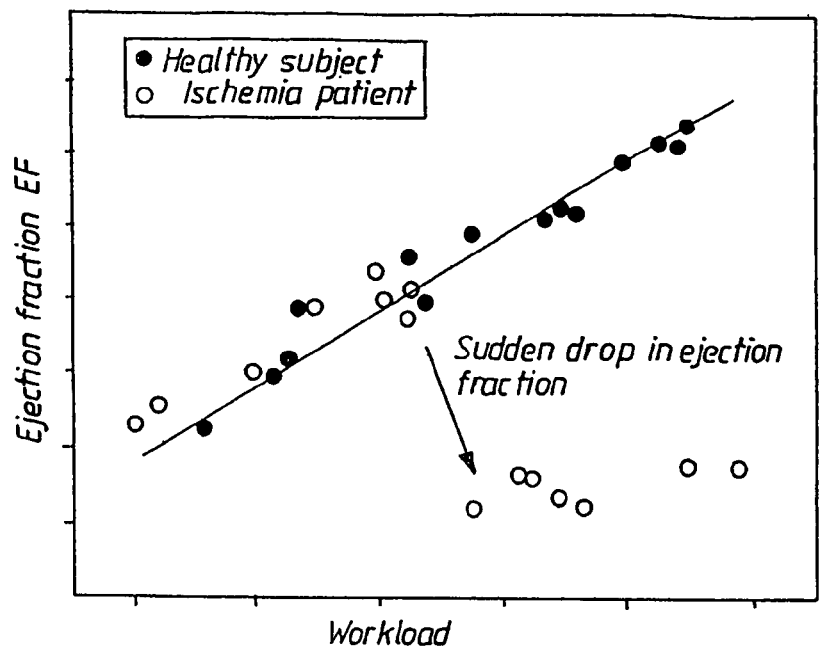
FIG. 2 is a graph qualitatively showing the ejection fraction (EF) as a function of workload for a healthy subject and for a subject suffering from ischemia.

FIG. 2 shows qualitatively EF as a function of the workload, represented by the heart rate, for a normal subject and for a patient experiencing ischemia. The sudden drop in EF shown in the figure is an indication of an ischemia of the patient in question.

The invention is based on tracking EF as a function of workload and detect sudden drops of EF at sufficiently high workload levels. The development of EF as a function of workload is then compared with a stored predetermined reference relation between EF and workload for the patient, which reference relation has been determined before the patient was affected by ischemia, cf. FIG. 2. It should be emphasized that this reference relation is specific for each patient and must be determined separately for each individual patient. Workload level and EF are stored in a memory as a digital signal. A quotient forming means is provided to form from this stored signal the quotient between a change in EF and corresponding change in the workload, and a quotient comparison means is provided for comparing said quotient with a predetermined quotient reference value for the detection of an ischemia. Alternatively a differentiating means is preferably provided to determine the derivative of EF with respect to workload by differentiating these stored signals to detect sudden drops of EF. If the derivative exceeds a predetermined limit value occurrence of ischemia is indicated.

Since a patient may experience, especially silent ischemia, under conditions for which no ischemia was detected e.g. a week ago, the oldest stored values should be discarded when new values of EF and workload are supplied to the memory. This is realized by a circular buffer of a fixed size, capable of storing a predetermined number of values.

Suitable threshold values for deviations from "normal" EF values, obtained for a healthy subject, for indicating an ischemia could be as follows.

1) Measured EF value deviates from the "normal" EF value by 3 times the standard deviation for EF;
2) A sudden drop of 5-10% in the measured EF when the workload is increased;
3) The measured absolute level of EF has dropped to 25-30%.

In practice all three conditions above are checked and a detection of ischemia is detected if e.g. at least one of them is satisfied, or alternatively if more than one or all three conditions are fulfilled.

A heart attack is detected as a large decrease in the EF which is present even during rest conditions. If normal EF equals 60%, a relatively small heart attack can cause a mildly lowered EF to e.g. 40-45%. A moderate or strong heart attack can cause the EF to decrease to 30-40%, and a massive heart attack, or, more commonly, several smaller heart attacks may result in an EF in the range of 10-25%.

The workload of the patient can be measured by several different kinds of workload sensors. Thus the workload can be measured by e.g. an accelerometer, minute ventilation means, means for determining the intrinsic P-wave rate for patients having a healthy SA node, means for determining metabolic demand of the patient, or by any combination of these examples.

A surrogate of EF can be obtained according to the invention by using several different methodologies. One example of such a methodology is to detect the cardiac events the onset of QRS and the opening and closing of the aortic valve in order to calculate EF according to one of the following equations $$LVEF=0.84-0.64*PEP/LVET$$

$$LVEF=1.125-1.25*PEP/LVET$$

where PEP denotes the pre-ejection period from onset of QRS to opening of the aortic valve, and LVET the left ventricular ejection time from opening to closing of the aortic valve.

The onset of ejection can be detected from the IEGM. The opening and closing of the aortic valve—and thereby PEP and LVET—can be detected in several ways, e.g. by a CMES-sensor as discussed above. The CMES-sensor is a piezoelectric sensor, wherein the indifferent ring on the lead is coated by piezoelectric material, such that a signal received from this sensor contains both electric and pressure information. The pressure information thus received includes several components. In a certain frequency range the sensor is sensible to e.g. sound, i.e. it works as a microphone. The signal also contains the true pressure, pressure changes or the time derivative of the pressure. By suitable filtration of the sensor signal valve openings and closings can be detected, since a valve closing is associated with a significant pressure increase and sounds. This is illustrated in FIG. 3.

Figure 3:
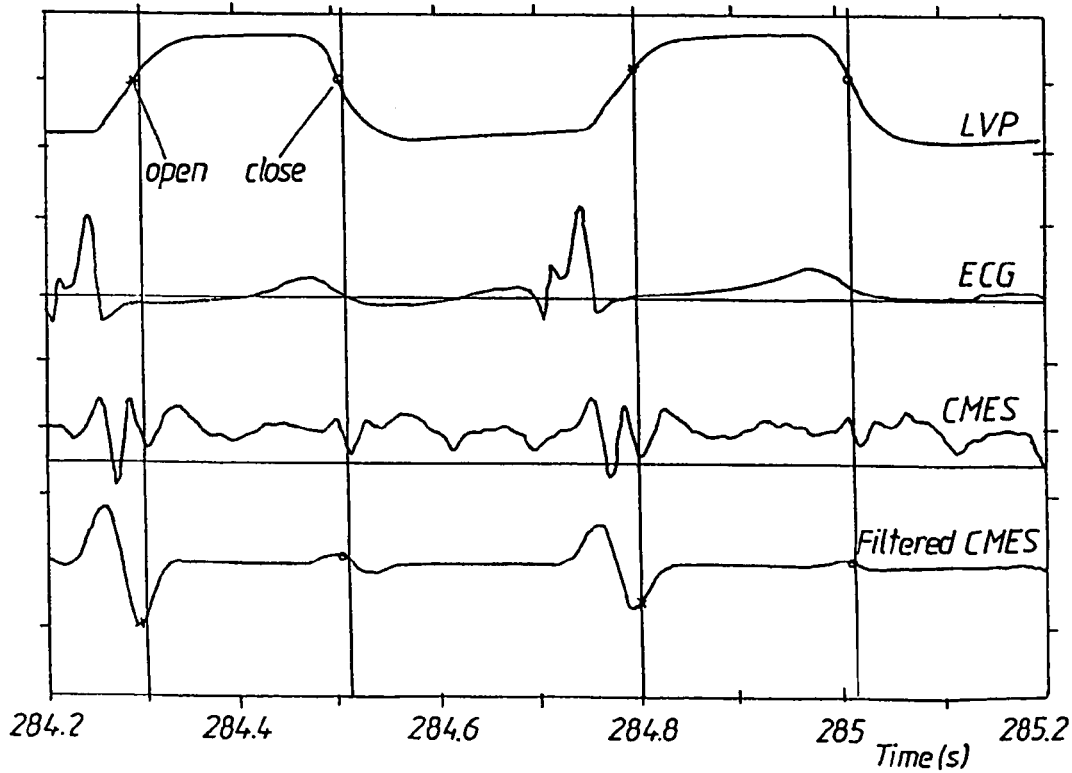
FIG. 3 qualitatively shows different measured signals as a function of time, which can be used for determining EF.

FIG. 3 thus shows the signal, on an arbitrary scale, obtained from a CMES-sensor in a cardiac vein on the left side of the heart as a function of time, together with measured left ventricular pressure, LVP, and a surface ECG. As appears from the indicated figures on the time axis the length of the shown diagram is 1 sec. The asterisks in the diagram mark the opening and the closing respectively of the aortic valve.

Another way to obtain a surrogate of EF is to use the amplitude of a cardiac impedance signal obtained from implanted leads. For a heart stimulator according to the invention ordinary leads for sensing and stimulating can preferably be used for this purpose. Since blood and tissue have different conduction properties, the impedance measured across the heart will depend on the blood filling of the heart.

Figure 4:
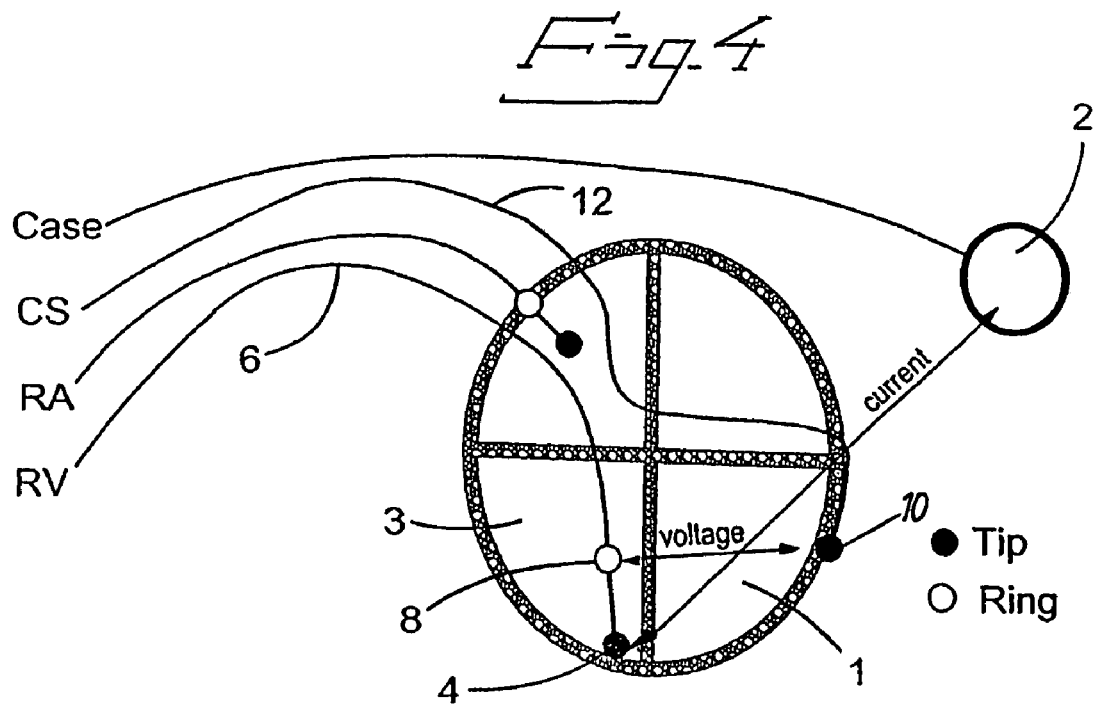
FIG. 4 illustrates a first embodiment for conducting an impedance measurement to determine a surrogate of EF according to the invention.
Figure 5:
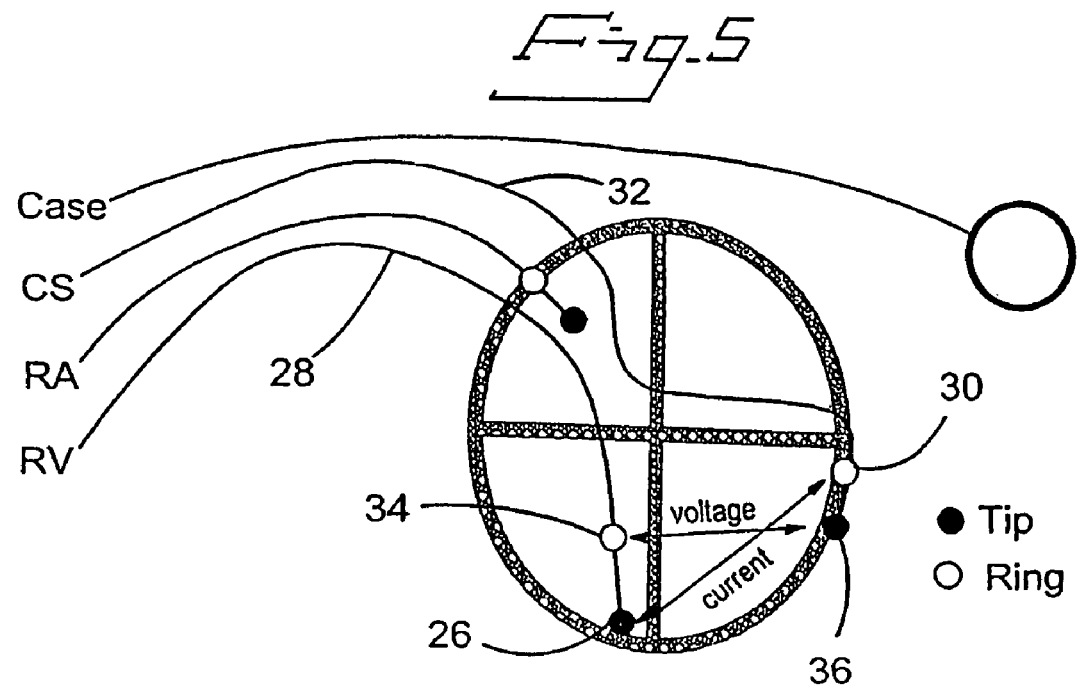
FIG. 5 illustrates a second embodiment for conducting an impedance measurement to determine a surrogate of EF according to the invention.

FIGS. 4 and 5 show two examples of electrode configurations suitable for obtaining a left ventricular volume surrogate which can be used as an EF surrogate.

FIG. 4 thus illustrates an example of impedance measurements between left and right ventricles 1, 3 of a patient's heart. A current is supplied between the pacemaker case, schematically shown at 2, and the tip electrode 4 of a right ventricular lead 6, and the resulting voltage is measured between the ring electrode 8 of the ventricular lead 6 and the tip electrode 10 of a unipolar coronary sinus or left ventricular lead 12.

FIG. 5 illustrates another embodiment wherein current is supplied between the tip electrode 26 of a bipolar right ventricular lead 28 and the ring electrode 30 of a bipolar coronary sinus lead 32, and the resulting voltage is measured between the ring electrode 34 of the right ventricular lead 28 and the tip electrode 36 of the coronary sinus or left ventricular lead 32.

If no left ventricular lead is present—which would be rare for the heart stimulators for the population of patients in question—a surrogate of EF can be obtained by using only the right ventricular lead.

If an ischemia is detected actions must be taken, like alerting a physician or a clinic or simply storing the event in a database storing patient diagnostics. Such actions require communication with systems like Housecall and consequently means for telemetry communication. Means could also be provided for alerting the patient himself or herself to come under medical treatment as soon as possible. Such an alerting function is of special importance for patients suffering from a silent ischemia, viz. patients who are not feeling anything of the detected ischemia. The patient could then also be instructed not to drive to the emergency room himself or herself.

Another example of actions is to change operation parameters of the heart stimulator which includes the ischemia detector. A patient experiencing ischemia needs to prolong the period of diastole to increase the flow of blood to the cardiac cells. Appropriate actions could therefore be to decrease the stimulation base rate, decrease the maximum tracking rate, making the workload sensor less sensitive, etc. The heart stimulator according to the invention therefore comprises stimulation controlling means for automatically controlling the delivery of stimulation pulses to the patient's heart in response to the detection of an ischemia. The changes could either be permanent or reset after a certain period of time. In an implantable cardioverter defibrillator parameters of ventricular tachycardia and ventricular fibrillation detection could also be changed to make it more sensitive, as ischemia sometimes precedes arrhythmic events. If such parameters are changed—permanently or temporarily—this must be recorded and communicated to the physician by means of the programmer at next follow-up.

Although modifications and changes may be suggested by those skilled in the art, it is the invention of the inventors to embody within the patent warranted heron all changes and modifications as reasonably and properly come within the scope of their contribution to the art.

We claim as our invention:

1. An ischemia detector comprising:
   a workload sensor configured to interact with a patient to sense a workload of the patient;
   an ejection fraction (EF) determining unit that determines an ejection fraction associated with the heart of the patient;
   a storage unit that stores a predetermined reference relation between EF and workload for the patient; and
   an analyzing unit that identifies a state of ischemia of the patient dependent on a deviation of EF determined by said EF determining unit for respective workloads of the patient from the stored reference relation.

2. An ischemia detector as claimed in claim 1 wherein said EF determining unit comprises an EF sensor that senses a parameter representative of EF, and a calculation unit that calculates EF for the patient from said parameter.

3. An ischemia detector as claimed in claim 1 wherein said EF sensor is a CMES sensor.

4. An ischemia detector as claimed in claim 1 wherein said EF sensor is a pressure sensor.

5. An ischemia detector as claimed in claim 1 wherein said EF sensor is a photo-plethysmograph.

6. An ischemia detector as claimed in claim 1 wherein said EF sensor is an impedance measuring arrangement configured to measure an impedance across the heart of the patient.

7. An ischemia detector as claimed in claim 6 wherein said impedance measuring arrangement comprises leads configured for implantation into the heart of the patient.

8. An ischemia detector as claimed in claim 1 wherein said workload sensor comprises an accelerometer.

9. An ischemia detector as claimed in claim 1 wherein said workload sensor comprises an arrangement for determining minute ventilation of the patient.

10. An ischemia detector as claimed in claim 1 wherein said workload sensor comprises a P-wave rate detector.

11. An ischemia detector as claimed in claim 1 wherein said workload sensor comprise an arrangement that determines metabolic demand of the patient.

12. An ischemia detector as claimed in claim 1 wherein said analyzing unit comprises a quotient forming unit that forms a quotient between a change in EF and a corresponding change in the workload, and a quotient comparator that compares said quotient with a predetermined quotient reference value.

13. An ischemia detector as claimed in claim 1 comprising a derivative former that determines a derivative of EF with respect to said workload, and a derivative comparator that compares said derivative with a predetermined derivative reference value.

14. An ischemia detector as claimed in claim 1 comprising a circular buffer that stores a predetermined number of analysis results from said analyzing unit.

15. An ischemia detector as claimed in claim 1 wherein said EF determining unit identifies an onset of QRS and opening and closing of the aortic valve of the heart of the patient.

16. An ischemia detector as claimed in claim 15 wherein said EF determining unit determines left ventricular ejection fraction (LEVF) from an equation selected from the group consisting of $$LVEF = 0.84 - 0.64 * PEP/LVET$$

$$LVEF = 1.125 - 1.25 * PEP/LVET$$

wherein PEP is a pre-ejection period from said onset of QRS to said opening of the aortic valve, and LVET is a left ventricular ejection time from said opening of the aortic valve to said closing of the aortic valve.

17. An ischemia detector as claimed in claim 1 comprising an alerting unit that emits an output signal in response to detection of said state of ischemia by said analyzing unit.

18. A heart stimulator comprising:
   an ischemia detector comprising a workload sensor configured to interact with a patient to sense a workload of the patient,
   an ejection fraction (EF) determining unit that determines an ejection fraction associated with the heart of the patient, a storage unit that stores a predetermined reference relation between EF and workload for the patient, and an analyzing unit that identifies a state of ischemia of the patient dependent on a deviation of EF determined by said EF determining unit for respective workloads of the patient from the stored reference relation;
   a stimulation pulse delivery arrangement configured to deliver stimulation pulses to the heart of the patient; and
   a control unit connected to said ischemia detector and to said stimulation pulse delivery arrangement that controls deliver of said stimulation pulses to the patient by said stimulation pulse delivery arrangement dependent on detection of said state of ischemia by said analyzing unit of said ischemia detector.

19. A heart stimulator as claimed in claim 18 comprising a stimulator housing, and wherein said stimulation pulse delivery arrangement comprises a bipolar right ventricular lead having a tip electrode and a ring electrode, and a left ventricular lead having a tip electrode, and wherein said EF determining unit of said ischemia detector comprises an impedance measuring arrangement that includes said bipolar right ventricular lead and said left ventricular lead, and a current source that supplies a current between the tip electrode of the right ventricular lead and said stimulator housing, and a voltage measuring arrangement that measures a voltage, resulting from said current, between said ring electrode of said right ventricular lead and said tip electrode of said left ventricular lead.

20. A heart stimulator as claimed in claim 18 wherein said stimulation pulse delivery arrangement comprises a bipolar right ventricular lead having a tip electrode and a ring electrode, and a bipolar left ventricular lead having a tip electrode and a ring electrode, and wherein said EF determining unit of said ischemia detector comprises an impedance measuring arrangement that includes said bipolar right ventricular lead and said bipolar left ventricular lead, and a current source that applies a current between the tip electrode of the right ventricular lead and the ring electrode of the left ventricular lead, and a voltage measuring arrangement that measures a voltage, resulting from said current, between the ring electrode of the right ventricular lead and the tip electrode of the left ventricular lead.

21. A method for detecting a state of ischemia of a patient comprising the steps of:
- detecting a parameter indicative of ejection fraction (EF) of the heart of the patient;
- detecting a parameter indicative of workload of the patient;
- identifying a predetermined reference relation between EF and workload for the patient; and
- detecting a state of ischemia of the patient from deviations in EF for respective workloads from said predetermined reference relation.

22. A method as claimed in claim 21 comprising forming a quotient between a change in EF and a corresponding change in said workload, and comparing said quotient with a predetermined quotient reference value.

23. A method as claimed in claim 21 comprising forming a derivative of EF with respect to workload, and comparing said derivative with a predetermined derivative reference value.

24. A method as claimed in claim 21 comprising determining onset of QRS and opening and closing of the aortic value of the heart of the patient, and calculating left ventricular ejection fraction (LVEF) from an equation selected from the group consisting of $$LVEF = 0.84 - 0.64 * PEP/LVET$$

$$LVEF = 1.125 - 1.25 * PEP/LVET$$

wherein PEP is a pre-ejection period from said onset of QRS to said opening of the aortic valve, and LVET is a left ventricular ejection time from said opening of the aortic valve to said closing of the aortic valve.

25. A method as claimed in claim 21 comprising storing an occurrence of detection of said state of ischemia of the patient in a data base, accessible for subsequent analysis.

* * * * *